(12) United States Patent
Plos et al.

(10) Patent No.: US 7,367,993 B2
(45) Date of Patent: May 6, 2008

(54) DYEING COMPOSITIONS COMPRISING AT LEAST ONE 1,3-INDANDIONE DERIVATIVE

(75) Inventors: Grégory Plos, Tokyo (JP); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 209 days.

(21) Appl. No.: 11/151,269

(22) Filed: Jun. 14, 2005

(65) Prior Publication Data

US 2005/0283922 A1 Dec. 29, 2005

Related U.S. Application Data

(60) Provisional application No. 60/637,749, filed on Dec. 22, 2004.

(30) Foreign Application Priority Data

Jun. 14, 2004 (FR) .................................. 04 51167

(51) Int. Cl.
*A61K 7/13* (2006.01)
(52) U.S. Cl. ...................... 8/405; 8/406; 8/407; 8/408; 8/410; 8/421; 8/607; 568/303
(58) Field of Classification Search ................ 8/405, 8/406, 407, 408, 410, 421, 607; 568/303
See application file for complete search history.

(56) References Cited

FOREIGN PATENT DOCUMENTS

| DE | 43 17 855 A1 | 12/1994 |
|----|---|---|
| DE | 43 35 627 A1 | 4/1995 |
| DE | 43 35 628 A1 | 4/1995 |
| DE | 197 17 222 A1 | 10/1998 |
| DE | 197 45 355 A1 | 4/1999 |
| DE | 198 45 481 A1 | 4/2000 |
| EP | 1 010 419 A2 | 6/2000 |
| EP | 1 013 259 A1 | 6/2000 |
| EP | 1 300 134 A2 | 4/2003 |
| WO | WO 95/11001 | 4/1995 |
| WO | WO 99/18914 | 4/1999 |

OTHER PUBLICATIONS

Ozolina, V.; Neilands, Journal of Russian (Analogs of 2-methoxycarbonyl-1,3-indandione), 1971 (STIC Search Report).*
STIC Search Report dated Apr. 25, 2007.*
French Search Report for FR 0451167 (French priority application for the present application), dated Jan. 20, 2005.
European Search Report for EP 05 29 1274 (European counterpart to present U.S. Appl. No. 11/151,269), dated Oct. 17, 2005.
Richard R. Hark et al.; "Synthetic Studies of Novel Ninhydrin Analogs," Canadian Journal of Chemistry, vol. 79, No. 11, pp. 1632-1654 (2001).
B. Nalliah et al., "The Total Synthesis of (±) Ochrobirine," Canadian Journal of Chemistry, vol. 50, No. 12, pp. 1819-1824 (1972).
Madeleine M. Joullié et al., "Ninhydrin and Ninhydrin Analogs. Syntheses and Applications," Tetrahedron, vol. 47, No. 42, pp. 8791-8830 (1991).
Richard R. Hark, "Synthesis of Ninhydrin Analogues," A Dissertation in Chemistry, University of Pennsylvania, pp. 1-575 (1996).
English language abstract of DE 43 17 855 A1, Dec. 1, 1994.
English language abstract of DE 43 35 627 A1, Apr. 20, 1995.
English language abstract of DE 43 35 628 A1, Apr. 20, 1995.
English language abstract of DE 197 45 355 A1, Apr. 15, 1999.
English language abstract of DE 198 45 481 A1, Apr. 6, 2000.
English language abstract of EP 1 010 419 A2, Jun. 21, 2000.
English language abstract of EP 1 013 259 A1, Jun. 28, 2000.
English language abstract of EP 1 300 134 A2, Apr. 9, 2003.

* cited by examiner

*Primary Examiner*—Eisa Elhilo
(74) *Attorney, Agent, or Firm*—Finnegan, Henderson, Farabow, Garrett & Dunner, LLP

(57) ABSTRACT

The present disclosure relates to compositions for dyeing keratin materials, for example, compositions for hair dyeing comprising at least one 1,3-indandione derivative, a method for dyeing using such compositions and a multicomponent dyeing agent used for carrying out such a method.

The present disclosure makes it possible, for example, to obtain a color of the keratin fibers which is fast, resistant to light and to washing.

35 Claims, No Drawings

DYEING COMPOSITIONS COMPRISING AT LEAST ONE 1,3-INDANDIONE DERIVATIVE

CROSS-REFERENCE TO RELATED APPLICATION

This application claims benefit of U.S. Provisional Application No. 60/637,749, filed Dec. 22, 2004, the contents of which are incorporated herein by reference. This application also claims benefit of priority under 35 U.S.C. § 119 to French Patent Application No. 04 51167, filed Jun. 14, 2004, the contents of which are also incorporated by reference.

FIELD OF THE INVENTION

The present disclosure relates to compositions for dyeing keratin materials, such as compositions for hair dyeing, comprising at least one 1,3-indandione derivative, a method for dyeing using such compositions and a multicomponent dyeing agent used for carrying out such a method.

BACKGROUND OF THE INVENTION

For a long time, many people have sought to modify the color of their skin, of their eyelashes or of their hair, for example, to mask their grey hair. To do this, several technologies have been developed.

It is known to dye human keratin fibers, such as the hair, with dyeing compositions containing oxidation dye precursors, generally called oxidation bases. These oxidation bases are colorless or slightly colored compounds which, when combined with oxidizing agents, give rise, through a process of oxidative condensation, to colored compounds. These colored compounds are insoluble and are trapped inside the hair fiber.

It is also known that it is possible to vary the shades obtained with these oxidation bases by combining them with couplers or color modifiers. The variety of molecules used at the level of the oxidation bases and the couplers allows a rich palette of colors to be obtained.

The colors obtained may exhibit good fastness to shampoo. However, the oxidation reaction occurs with the aid of oxidizing agents such as hydrogen peroxide in a basic medium. These oxidizing agents attack the keratin of the hair, such that the cosmetic and mechanical properties of the hair can deteriorate considerably in the event of repeated dyeing.

It is also known to dye human keratin fibers by direct dyeing, which comprises applying to the keratin fibers direct dyes which are colored and dyeing molecules having affinity for the fibers. There may be mentioned, by way of examples of direct dyes which are conventionally used, nitro dyes, benzene dyes, anthraquinone dyes, nitropyridine dyes, azo dyes, cationic azo dyes, xanthene dyes, acridine dyes, azine dyes or dyes of the triarylmethane type or natural dyes.

Other method(s) exist for dyeing keratin materials using indandiones such as 1,2-indandiones and 1,3-indandiones. Such dyeing method(s) are, for example, described in the following Patent Applications: EP 1 010 419, EP 1 013 259, EP 1 300 134, WO 95/11001 and WO 99/18914. The colors thus obtained may be very chromatic and may not bring about chemical degradation of keratin, but at the same time may have the disadvantage of being only temporary or semipermanent, i.e., the colors may fade after only 4 to 5 shampooings.

A need therefore remains for compositions and methods for dyeing which allow good fastness to be obtained without involving the use of oxidizing agents which are likely to damage keratin materials.

DESCRIPTION OF THE INVENTION

Therefore, disclosed herein are novel dyeing compositions which make it possible to dye keratin materials, such as the hair, with fastness equivalent or even superior to that obtained by oxidation dyeing, in the absence of strong oxidizing agents, thereby preserving the keratin materials.

More specifically, disclosed herein is a composition for dyeing keratin materials such as the skin and the keratin fibers comprising, in an appropriate medium, at least one 1,3-indandione derivative chosen from compounds of formulae (I), (II) and (III)

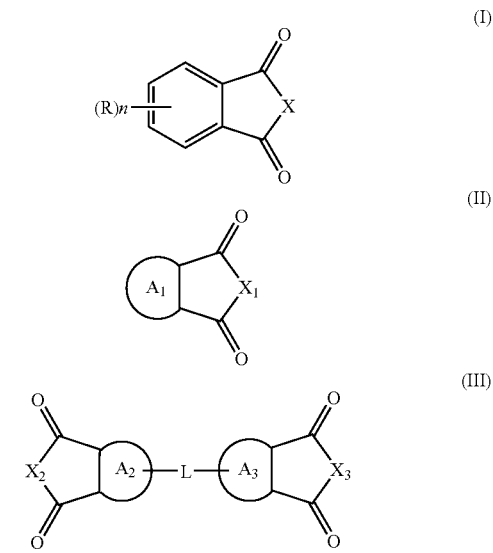

wherein
  $X$, $X_1$, $X_2$ and $X_3$, which may be identical or different, are each a radical $CR_1 R_2$,
    wherein $R_1$ and $R_2$, which may be identical or different, are each chosen from a hydrogen atom, halogen atoms, $C_3$-$C_{18}$ alkyl radicals, $C_2$-$C_{18}$ alkenyl radicals, a carboxyl radical, hydroxycarbonylalkyl radicals, a hydrogenocarbonyl radical, hydrogenocarbonylalkyl radicals, alkylcarboxyalkyloxy radicals, a cyano radical, a thiocyano radical, a nitro radical, a nitroso radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, aryl radicals, heteroaryl radicals, and quaternary ammonium radicals such as tetraalkylammonium, pyridinium, benzothiazolium and imidazolium,
  $A_1$ is chosen from fused and non-fused polyaromatic radicals comprising from 6 to 50 carbon atoms, which may comprise at least one heteroatom chosen from nitrogen, sulphur, oxygen, and phosphorus,
  $A_2$ and $A_3$, which may be identical or different, are each chosen from fused and non-fused, mono- and polyaromatic radicals comprising from 6 to 50 carbon atoms, which may comprise at least one heteroatom chosen from nitrogen, sulphur, oxygen, and phosphorus, L is a single bond or an aliphatic or aromatic divalent radical, which may comprise at least one heteroatom chosen from oxygen, sulphur, nitrogen and phosphorus and may be fused with at least one of $A_2$ and $A_3$;

n is an integer chosen from 0 to 4, i.e., n=0, 1, 2, 3, or 4;

R is chosen from halogen atoms, alkyl radicals, $C_2$-$C_{18}$ alkenyl radicals, a carboxyl radical, alkoxycarbonyl radicals, hydroxycarbonylalkyl radicals, a hydrogenocarbonyl radical, hydrogenocarbonylalkyl radicals, alkylcarboxylalkyloxy radicals, a cyano radical, a thiocyano radical, a nitro radical, a nitroso radical, a sulphonato radical, alkylsulphonamido radicals, a hydroxyl radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, a silyl radical, alkylsilyl radicals, alkylarylsilyl radicals, arylsilyl radicals, a siloxyl radical, alkylsilyloxy radicals, arylsilyloxy radicals, aryl radicals, heteroaryl radicals, quaternary ammonium radicals, a radical of the formula

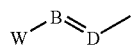

wherein B and D, which may be identical or different, are each chosen from carbon and nitrogen atoms and W is chosen from a ring of at least 5 members and aromatic and heteroaromatic, fused and non-fused polycycles, wherein the heteroatom may be chosen from nitrogen, oxygen, sulphur, and phosphorus, with the following provisos:

when X is a radical $CR_1R_2$ and $R_1$ and $R_2$ are each a hydrogen atom, the compound of formula (I) is of the following formula

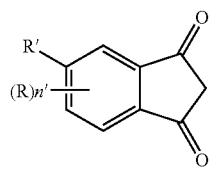

wherein n' is equal to 0, 1, 2 or 3, and R' is as defined for R but is not a methoxy radical or a chloro radical, when X is a radical $CR_1R_2$, n is equal to 0 and $R_1$ is a hydrogen atom, then $R_2$ is chosen from halogen atoms and substituted alkyl radicals comprising from 1 to 4 carbon atoms, and when X is a radical $CR_1R_2$, n is equal to 0 and $R_1$ is OH, then $R_2$ is not an amino, alkylamino, dialkylamino, arylalkylamino, diarylamino or alkenylamino radical.

The colors thus obtained may exhibit good chromaticity and may be distinguishable, for example, by good fastness to external agents such as light, shampoos and sweat. Such compositions are, for example, useful for dyeing keratin fibers, such as the hair.

In the above description, the number of carbons ranging from 1 to 18 corresponds, unless otherwise stated, to the number of carbons of the alkyl radical. In at least one embodiment, the alkyl radical or the derivative thereof comprises from 1 to 10 carbon atoms, such as from 1 to 6 carbon atoms.

When the radical indicated corresponds to an aryl radical, then the number of carbons ranges, for example, from 6 to 30.

As used herein, a "polyaromatic radical" means a radical comprising at least two aromatic rings, wherein the rings of the radical may be fused or non-fused. A "monoaromatic radical" is a radical comprising a single aromatic ring.

In formula (I) above, R is, for example, chosen from halogen atoms, alkyl radicals, aryl radicals, alkoxy radicals, aryloxy radicals, a carboxyl radical, alkoxycarbonyl radicals, nitro, amino, mono- and dialkylamino radicals, a cyano radical, a thiocyano radical, a sulphonato radical, and alkylsulphonamido radicals. Or, in at least one embodiment, n is equal to 0.

In at least one embodiment, R' is a bromine atom or an alkyl radical.

In at least one embodiment, $R_1$ and $R_2$, which may be identical or different, are each chosen from a hydrogen atom, halogen atoms, such as a bromine atom, alkoxy radicals, and alkyl radicals.

In the compounds of formula (II) or (III), the rings $A_1$ are, for example, chosen from naphthalene, anthracene, thiophene, pyridine and quinoline rings.

The rings $A_2$ and $A_3$ are, for example, chosen from benzene, naphthalene, anthracene, thiophene, pyridine and quinoline rings. In one embodiment, $A_2$ and $A_3$, which may be identical or different, are each chosen from benzene, naphthalene, thiophene, and pyridine rings.

In another embodiment, $A_1$, $A_2$ and $A_3$ are chosen so as to form, with the indandione ring, a system of delocalized π electrons.

The rings $A_1$, $A_2$ and $A_3$ as disclosed herein may be substituted or unsubstituted. By way of examples of substituents for these rings, there may be mentioned the atoms and radicals given in the definition of R.

By way of example of compounds of formula (I), there may be mentioned

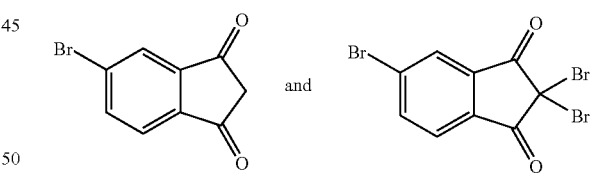

The compounds of formula (I), in at least one embodiment, are chosen from those of the following formula:

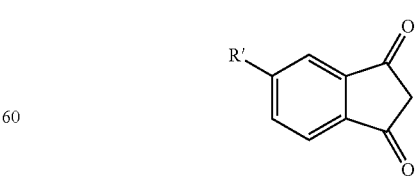

wherein R' is chosen from a bromine atom, alkyl radicals, aryl radicals, alkoxy radicals except methoxy, aryloxy radicals, a carboxyl radical, alkoxycarbonyl radicals, nitro, amino, mono- and dialkylamino radicals, a cyano radical, a thiacyano radical, a sulphonato radical, and alkylsulphonamido radicals.

By way of example of the compounds of formula (II), there may be mentioned

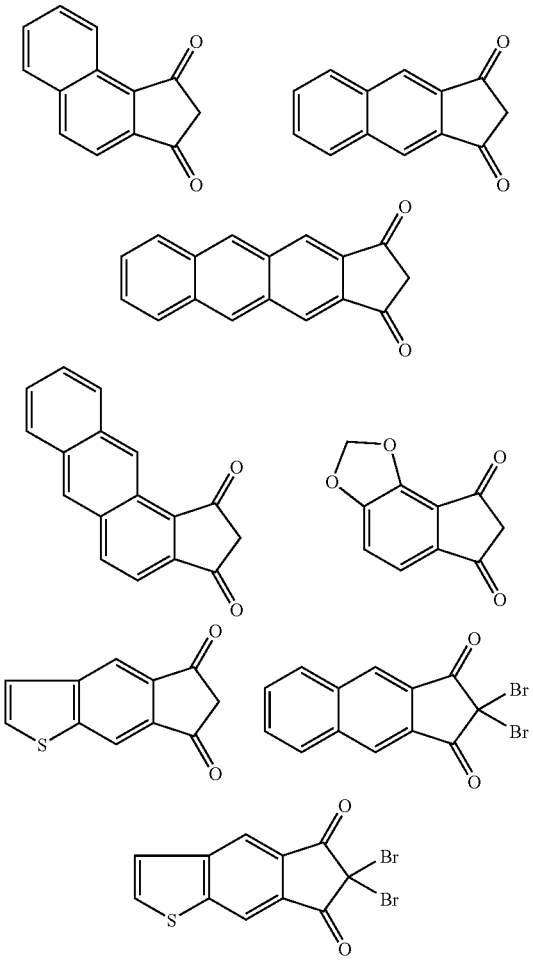

The 1,3-indandione derivatives of formula (II), in at least one embodiment, are chosen from the following compounds:

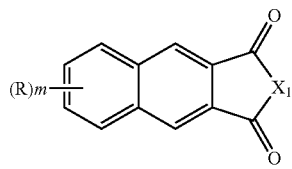

wherein $X_1$ is a $CR_1R_2$ radical as defined above, R is as defined above, m ranges from 0 to 6, such as from 0 to 4. In one embodiment, m is equal to 0. Further, for example, R is chosen from halogen atoms, alkyl radicals, and alkoxy radicals.

In one embodiment, $R_1$ and $R_2$, which may be identical or different, are each chosen from a hydrogen atom, halogen atoms, alkyl radicals, and alkoxy radicals.

The compounds of formula (III), in at least one embodiment, are of the following formula

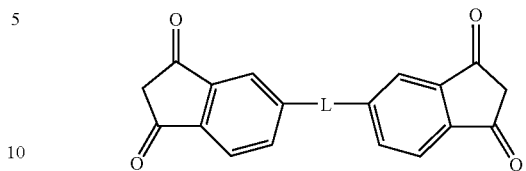

As disclosed herein, L may, for example, be a ring of at least 6 members or an aromatic or heteroaromatic, fused or non-fused polycycle, wherein these rings may be substituted. L may also form a ring fused with at least one of $A_2$ and $A_3$.

By way of examples of compounds of formula (III), there may be mentioned

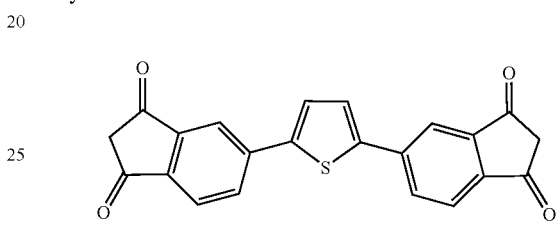

As disclosed herein, the groups L, $R_1$, $R_2$, R, $A_1$, $A_2$ and $A_3$ may independently be substituted or unsubstituted. When they are substituted, the at least one substituent may be chosen from halo, $C_1$-$C_6$ alkyl, hydroxyl, $C_1$-$C_6$ alkoxy, amino, imidazolyl, pyridinyl, mono- or di($C_1$-$C_6$ alkyl)amino, mono- or dihydroxy($C_1$-$C_6$ alkyl)amino or tri($C_1$-$C_6$ alkyl)ammmonio radicals, thio, ($C_1$-$C_6$ alkyl)thio, thio($C_1$-$C_6$ alkyl), ($C_1$-$C_6$ alkyl)carbonyl, hydrogenocarbonyl, hydroxycarbonyl, ($C_1$-$C_6$ alkoxy)carbonyl, nitro, and sulphonate groups and the corresponding protonated groups such as ammonio, imidazolio and pyridinio groups.

The presently disclosed compounds of formula (I), (II) or (III) also include the corresponding acid addition salts thereof and the base addition salts thereof.

In the radicals defined above, the alkyl radicals comprise, for example, from 1 to 10 carbon atoms.

The 1,3-indandione derivatives of formula (I), (II) or (III) may be obtained from known methods of synthesis. For example, the syntheses may be performed based on the teaching described in the documents EP 1 010 419, EP 1 013 259, EP 1 300 134, WO 95/11001 and WO 99/18914 and in the articles "Ninhydrin and ninhydrin analogs, Syntheses and applications", M. M. Joullié, T. R. Thompson, N. H. Nemeroff, Tetrahedron, Vol. 47, No. 42, 8791-8830 (1991), "The total synthesis of Ochrobirine", B. Nalliah, Q. A. Ahmed, R. H. F. Manske, R. Rodrigo, Canadian Journal of Chemistry, 50, 1819 (1972), Synthesis of Ninhydrin analogs, R. R. Hark, PhD, Dissertation in chemistry, University of Pennsylvania, 1996.

As disclosed herein, the 1,3-indandione derivatives of formula (I), (II), or (III) described above may be used alone for dyeing keratin materials. Indeed, these compounds are capable of generating colored molecules with the amine functional groups of keratin (colored reaction).

It may also be possible to use the compounds of formula (I), (II), or (III) together with at least one activator which makes it possible to modify the kinetics of reaction of the 1,3-indandione derivative with the keratinous material. Such an activator may be an oxidizing agent, a reducing agent, Brönsted acids, a metal catalyst such as catalysts based on a transition metal such as iron, platinum and palladium, proteins, such as enzymes, compounds which modify the ionic strength of the medium, such as NaCl salts, compounds comprising at least one labile hydrogen chosen from those comprising at least one functional group chosen from primary and secondary amine functional groups and those comprising at least one activated methylene functional group. It is also possible to use a mixture of such compounds.

In one embodiment, the chemical activator is a compound comprising at least one labile hydrogen chosen from the compounds comprising at least one functional group chosen from primary and secondary amino functional groups and the compounds comprising at least one activated methylene functional group. For example, the compounds with a primary amine or a secondary amine functional group are aromatic amines.

There may be mentioned, by way of examples of such aromatic amines,
N,N-dimethyl-p-phenylenediamine,
N,N-diethyl-p-phenylenediamine,
N-(2-hydroxyethyl)-N-ethyl-p-phenylenediamine,
N,N-bis(2-hydroxyethyl)-p-phenylenediamine,
N-(2-methoxyethyl)-p-phenylenediamine,
2,3-, 2,4- or 2,5-dichloro-p-phenylenediamine,
2-chloro-p-phenylenediamine
dibromohydrate of 2,5-dihydroxy-4-morpholinoaniline,
2,3- or 4-aminophenol,
2-aminomethyl-4-aminophenol,
-2-hydroxymethyl-4-aminophenol,
ortho-phenylenediamine,
para-phenylenediamine,
ortho-toluenediamine,
2,5-diaminotoluene,
2,5-diaminophenol,
2,5-diaminophenethol,
4-amino-3-methylphenol,
2-(2,5-diaminophenyl)ethanol,
2,4-diaminophenoxyethanol,
2-(2,5-diaminophenoxy)ethanol,
4-methylaminoaniline,
3-amino-4-(2'-hydroxyethyloxy)aniline,
3,4-methylenediaminoaniline,
3,4-methylenedioxyaniline,
3-amino-2,4-dichlorophenol,
4-methylaminophenol,
2-methyl-5-aminophenol,
3-methyl-4-aminophenol,
2-methyl-5-(2-hydroxyethylamino)phenol,
6-methyl-3-amino-2-chlorophenol,
2-methyl-5-amino-4-chlorophenol,
3,4-methylenedioxyphenol,
5-(2-hydroxyethylamino)-4-methoxy-2-methylphenol,
4-amino-2-hydroxymethylphenol,
1,3-diamino-2,4-dimethoxybenzene,
2-, 3-, 4-aminobenzoic acid,
2-amino-, 3-amino- or 4-aminophenylacetic acid,
2,3-, 2,4-, 2,5-, 3,4- or 3,5-diaminobenzoic acid,
4-amino- or 5-aminosalicylic acid,
3-amino-4-hydroxybenzoic acid,
4-amino-3-hydroxybenzoic acid,
2-amino-, 3-amino- or 4-aminobenzenesulphonic acid,
3-amino-4-hydroxybenzenesulphonic acid,
4-amino-3-hydroxynaphthalene-1-sulphonic acid,
6-amino-7-hydroxynaphthalene-2-sulphonic acid,
7-amino-4-hydroxynaphthalene-2-sulphonic acid,
4-amino-5-hydroxynaphthalene-2,7-disulphonic acid,
3-amino-2-naphthoic acid,
3-aminophthalic acid,
5-aminoisophthalic acid,
1,3,5-triaminobenzene,
1,2,4-triaminobenzene,
1,2,4,5-tetraaminobenzene,
2,4,5-triaminophenol,
pentaaminobenzene,
hexaaminobenzene,
2,4,6-triaminoresorcinol,
4,5-diaminopyrocatechol,
4,6-diaminopyrogallol,
3,5-diamino-4-hydroxypyrocatechol, and
aromatic anilines and aromatic phenols comprising another aromatic residue, corresponding to formula (Ia)

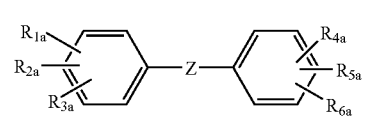

wherein
$R_{1a}$ is chosen from hydroxyl and amino groups optionally substituted with at least one group chosen from $C_1$-$C_4$ alkyl, $C_1$-$C_4$ hydroxyalkyl and ($C_1$-$C_4$ alkoxy)-($C_1$-$C_4$ alkyl) groups,
$R_{2a}$, $R_{3a}$, $R_{4a}$, $R_{5a}$ and $R_{6a}$, which may be identical or different, are each chosen from a hydrogen atom, a hydroxyl group, and an amino group, optionally substituted with at least one group chosen from $C_1$-$C_4$ alkyl, $C_1$-$C_4$ hydroxyalkyl, and ($C_1$-$C_4$ alkoxy)-($C_1$-$C_4$ alkyl) groups, and carboxylic and sulphonic acid groups,
Z is chosen from a direct bond, a $C_1$-$C_4$ hydrocarbon chain which is saturated or unsaturated and optionally hydroxylated, a carbonyl, sulphonyl or imino group, an oxygen or sulphur atom, and a group of formula Q-($CH_2$—P—$CH_2$-Q')$_o$ wherein P is a direct bond or a group —$CH_2$— or —CHOH—, Q and Q', which may be identical or different, are each chosen from an oxygen atom, a group $NR_7$ wherein $R_7$ is chosen from a hydrogen atom, and $C_1$-$C_4$ alkyl and $C_1$-$C_4$ hydroxyalkyl groups and groups O—($CH_2$)$_p$NH and NH—($CH_2$)$_p$'—O wherein p and p', which may be identical or different, are each 2 or 3, and o is a number ranging from 1 to 4.

The nonaromatic primary or secondary amines are chosen for example from
2-aminoethanol,
2-methoxyethylamine,
2-ethoxyethylamine,
2-(2-aminoethoxy)ethanol,
2- or 3-aminopropanol,
2,3-dihydroxypropylamine,
4-hydroxypropylamine,
2-aminopropane-1,3-diol,
2-amino-2-methylpropanol,
2-amino-2-methylpropane-1,3-diol,
2-amino-2-hydroxymethylpropane-1,3-diol,
tetrahydropentylamine,
pentahydroxyhexylamines such as glucamine, D-glucosamine, and D-galactosamine,
1,2-diaminoethane,
1,2-diaminopropane, 1,3-diaminopropane,
1,3-diamino-2-propanol,
2-(2-aminoethylamino)ethylamine,
2-(2-aminoethylamino)ethanol,
3-(2-aminoethylamino)propylamine and
3-(2-aminoethylamino)propanol.

The compounds comprising at least one activated methylene functional group are chosen, for example, from the following:
1,2,3,3-tetramethyl-3H-indolium iodide,
1,2,3,3-tetramethyl-3H-indolium p-toluenesulphonate,
1,2,3,3-tetramethyl-3H-indolium methanesulphonate,
1,3,3-trimethyl-2-methyleneindoline,
2,3-dimethylbenzothiazolium iodide,
2,3-dimethylbenzothiazolium p-toluenesulphonate,
rhodanine,
rhodanine-3-acetic acid,
1-ethyl-2-quinaldinium iodide,
1-methyl-2-quinaldinium iodide,
barbituric acid,
thiobarbituric acid,
1,3-dimethylthiobarbituric acid,
diethylthiobarbituiric acid,
oxindole,
3-indoxyl acetate,
coumarone and
1-methyl-3-phenyl-2-pyrazolinone.

These primary and secondary amines and these compounds comprising at least one activated methylene functional group and other compounds comprising at least one labile hydrogen are also described in Patent Applications DE 43 17 855, DE 197 17 222, DE 198 45 481 and DE 197 45 355.

When the 1,3-indandione derivatives of formula (I), (II) or (III) are used in combination with a primary or secondary amine or with a compound comprising at least one activated methylene functional group, these different reagents should be stored separately in order to avoid a premature color reaction. The reagents should then be brought into contact immediately before application to the hair by freshly mixing two compositions respectively comprising the 1,3-indandione derivatives and the compounds comprising at least one labile hydrogen. The reagents may also be brought directly into contact with the hair by applying the various reagents in succession.

Further disclosed herein is a multicomponent dyeing agent comprising
as a first component, a composition (a) comprising at least one 1,3-indandione derivative chosen from the compounds of formulae (I), (II) and (III), and
as a second component, a composition (b) comprising at least one activator which makes it possible to modify the kinetics of reaction of the 1,3-indandione derivative.

In one embodiment, the activator is chosen from compounds comprising at least one functional group chosen from primary and secondary amine functional groups and compounds comprising at least one activated methylene functional group, as described above.

This multicomponent dyeing agent is, for example, provided in the form of a multicompartment kit, with at least one first compartment comprising the composition (a) and at least one second compartment comprising the composition (b).

As disclosed herein, the dyeing composition comprises, in addition to the at least one 1,3-indandione derivative chosen from the compounds of formulae (I), (II) and (III), at least one cosmetic active ingredient.

The at least one cosmetic active ingredient present in the cosmetic compositions of the present invention is chosen from, for example, vitamins, saccharides, oligosaccharides, polysaccharides which are optionally hydrolyzed and/or optionally modified, amino acids, oligopeptides, peptides, proteins which are optionally hydrolyzed and/or optionally modified, polyamino acids, enzymes, fatty acids and alcohols which are optionally branched, animal, vegetable and mineral waxes, ceramides and pseudoceramides, hydroxylated organic acids, UV-screening agents, antioxidants and anti-free-radical agents, chelating agents, antidandruff agents, seborrhoea-regulating agents, soothing agents, cationic, anionic, nonionic or amphoteric surfactants, cationic, anionic, neutral or amphoteric polymers, silicones which are optionally organomodified, mineral, vegetable or animal oils, polyisobutenes and poly(a-olefins), fatty esters, anionic polymers in dissolved or dispersed form, nonionic polymers in dissolved or dispersed form, reducing agents, solvents, hair dyes such as direct dyes or oxidation dye precursors (bases and/or couplers) different from the compounds comprising at least one functional group chosen from primary and secondary amine functional groups, oxidants such as hydrogen peroxide optionally combined with persalts, pigments and mixtures thereof.

The at least one cosmetic active ingredient is, for example, present in an amount ranging from 0.001% to 50% by weight, such as from 0.01% to 20% by weight, and further such as from 0.1% to 10% by weight, relative to the total weight of the cosmetic composition.

In one embodiment, the at least one cosmetic active ingredient is chosen from surfactants and polymeric agents (polymers) of a nonionic, cationic, anionic or amphoteric nature.

The compositions disclosed herein have, for example, a pH ranging from 2 to 12, such as from 6 to 11.

The at least one 1,3-indandione derivative chosen from the compounds of formulae (I), (II) and (III) is present in an amount ranging, for example, from 0.0001% to 30% by weight, relative to the total weight of the composition.

The compounds comprising at least one labile hydrogen, when they are present in the composition as disclosed herein, are present in an amount ranging, for example, from 0.0001% to 30% by weight, relative to the total weight of the composition.

Further disclosed herein is a dyeing method comprising applying to a keratin material, such as keratin fibers, a composition as described above. This composition is left in contact with the keratin material for a time sufficient to obtain the desired color. This leave-in time generally ranges from 5 minutes to 1 hour, such as from 15 to 30 minutes. The colored reaction between the at least one 1,3-indandione derivative and the amine functional groups of the keratin or the compounds comprising at least one labile hydrogen which are present may be accelerated by heating after application to the keratin material. The heating temperature, for example, does not exceed 250° C., and for example, is less than or equal to 60° C.

After the desired color is obtained, the keratin material is, in some embodiments, rinsed and washed.

When compounds comprising at least one labile hydrogen such as primary or secondary amines or compounds comprising at least one activated methylene functional group are used, the application of the reagents taking part in the colored reaction may also be performed in two stages, in other words, it is possible to successively apply two different compositions, one composition (a) comprising at least one 1,3-indandione derivative chosen from the compounds of formulae (I), (II), and (III) and one composition (b) comprising at least one compound chosen from compounds comprising at least one functional group chosen from primary and secondary amine functional groups and compounds comprising at least one activated methylene functional group.

Further disclosed herein is a dyeing method comprising applying to the hair, one after the other, in any order, a composition (a) and a composition (b) as defined above for the multicomponent dyeing agent.

This separate application of the two reactive compositions may have the advantage of avoiding the handling of colored compositions and may thus reduce the risks of staining materials such as clothes.

In one embodiment, the dyeing method described above is a method for dyeing keratin fibers, such as the hair.

It is also possible to rinse the keratin fibers ("intermediate rinsing") between the application of the composition (a) and the application of the composition (b).

In a manner similar to that described above, it is possible to heat the keratin material to which at least one of the compositions (a) and (b) is applied.

Even further disclosed herein is the use of the compositions described above for dyeing keratin materials, such as the hair.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The following example is intended to illustrate the invention and not to be limiting thereof.

EXAMPLE

The following dyeing composition was prepared:

| | |
|---|---|
| 1,3-Indandione derivative of formula (a1) below | $10^{-2}$ mol % |
| Ethanol | 50% |
| NaOH | q.s. pH 7 |
| Distilled water | q.s. 100% |

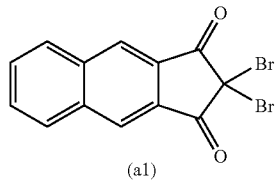

(a1)

The composition was applied to a lock of natural grey hair which was 90% white and to a lock of permanently waved grey hair which was 90% white for 30 minutes at a temperature of 60° C. After dyeing, the locks were rinsed and dried.

The calorimetric results are given in the table below:

| | Visual evaluation |
|---|---|
| Natural hair | coppery |
| Permanently waved hair | coppery |

What is claimed is:
1. A composition for dyeing a keratin material comprising:
   a medium appropriate for dyeing a keratin material and
   at least one 1,3-indandione derivative comprised in said medium in an amount sufficient for dyeing a keratin material and chosen from compounds of formulae (I), (II) and (III)

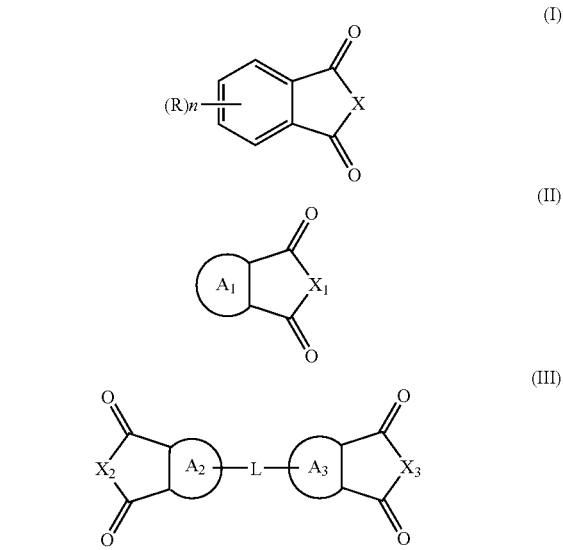

wherein
X, $X_1$, $X_2$ and $X_3$, which may be identical or different, are each a radical $CR_1R_2$,
    wherein $R_1$ and $R_2$, which may be identical or different, are each chosen from a hydrogen atom, halogen atoms, $C_3$-$C_{18}$ alkyl radicals, $C_2$-$C_{18}$ alkenyl radicals, a carboxyl radical, hydroxycarbonylalkyl radicals, hydrogenocarbonyl radicals, hydrogenocarbonylalkyl radicals, alkylcarboxyalkyloxy radicals, a cyano radical, a thiocyano radical, a nitro radical, a nitroso radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, aryl radicals, heteroaryl radicals, and quaternary ammonium radicals, $A_1$ is chosen from fused and non-fused polyaromatic radicals comprising from 6 to 50 carbon atoms, which may comprise at least one heteroatom chosen from nitrogen, sulphur, oxygen, and phosphorus, $A_2$ and $A_3$, which may be identical or different, are each chosen from fused and non-fused, mono- and polyaromatic radicals comprising from 6 to 50 carbon atoms, which may comprise at least one heteroatom chosen from nitrogen, sulphur, oxygen, and phosphorus, L is a single bond or an aliphatic or aromatic divalent radical, which may comprise at least one heteroatom chosen from oxygen, sulphur, nitrogen and phosphorus and may be fused with at least one of $A_2$ and $A_3$;

n is an integer chosen from 0, 1, 2, 3, and 4,

R is chosen from halogen atoms, alkyl radicals, alkenyl radicals, a carboxyl radical, alkoxycarbonyl radicals, hydroxycarbonylalkyl radicals, a hydrogenocarbonyl radical, hydrogenocarbonylalkyl radicals, alkylcarboxylalkyloxy radicals, a cyano radical, a thiocyano radical, a nitro radical, a nitroso radical, a sulphonato radical, alkylsulphonamido radicals, a hydroxyl radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, a silyl radical, $C_1$-$C_{18}$ alkylsilyl radicals, alkylarylsilyl radicals, arylsilyl radicals, a siloxyl radical, alkylsilyloxy radical, arylsilyloxy radical, aryl radicals, heteroaryl radicals, quaternary ammonium radicals, a radical of the formula

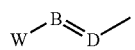

wherein B and D, which may be identical or different, are each chosen from carbon and nitrogen atoms and W is a ring of at least 5 members or an aromatic or heteroaromatic, fused or non-fused polycycle, wherein the heteroatom may be chosen from nitrogen, oxygen, sulphur and phosphorus, with the following provisos when X is a radical $CR_1R_2$ and $R_1$ and $R_2$ are each a hydrogen atom, the compound of formula (I) is of the following formula:

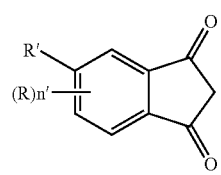

wherein n' is equal to 0, 1, 2 or 3, and R' is as defined for R but is not a methoxy radical or a chloro radical, when X is a radical $CR_1R_2$, n is equal to 0 and $R_1$ is a hydrogen atom, then $R_2$ is chosen from halogen atoms and substituted alkyl radicals comprising from 1 to 4 carbon atoms, and when X is a radical $CR_1R_2$, n is equal to 0 and $R_1$ is OH, then $R_2$ is not an amino, alkylamino, dialkylamino, arylalkylamino, diarylamino or alkenylamino radical.

2. The composition according to claim 1, wherein

R is chosen from halogen atoms, alkyl radicals, aryl radicals, alkoxy radicals, aryloxy radicals, a carboxyl radical, alkoxycarbonyl radicals, a nitro radical, an amino radical, monoalkylamino radicals, dialkylamino radicals, a cyano radical, a thiocyano radical, a sulphonato radical, and alkylsuiphonamino radicals, or n is equal to 0.

3. The composition according to claim 2, wherein R' is a bromine atom or an alkyl radical.

4. The composition according to claim 1, wherein $R_1$ and $R_2$, which may be identical or different, are each chosen from a hydrogen atom, halogen atoms, alkoxy radicals, and alkyl radicals.

5. The composition according to claim 1, wherein the compounds of formula (II) are such that the rings $A_1$ are chosen from naphthalene, anthracene, thiophene, pyridine and quinoline rings.

6. The composition according to claim 1, wherein the compounds of formula (III) are such that the rings $A_2$ and $A_3$ are chosen from benzene, naphthalene, anthracene, thiophene, pyridine and quinoline rings.

7. The composition according to claim 6, wherein the compounds of formula (III) are such that the rings $A_2$ and $A_3$ are chosen from benzene, naphthalene, thiophene and pyridine rings.

8. The composition according to claim 1, wherein $A_1$, $A_2$ and $A_3$ are chosen so as to form, with the indandione ring, a system of delocalized π electrons.

9. The composition according to claim 1, wherein the compounds of formula (I) are chosen from:

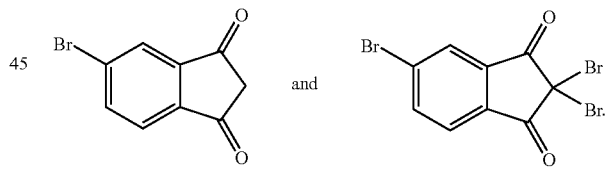

10. The composition according to claim 1, wherein the compounds of formula (I) are chosen from the compounds of the following formula:

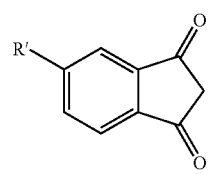

wherein R' is chosen from a bromine atom, alkyl radicals, aryl radicals, alkoxy radicals except a methoxy radical, aryloxy radicals, a carboxyl radical, alkoxycarbonyl radicals, a nitro radical, an amino radical, monodialkylamino radicals, dialkylamino radicals, a cyano radical, a thiacyano radical, a sulphonato radical and alkylsulphonamido radicals.

11. The composition according to claim 1, wherein the compounds of formula (II) are chosen from:

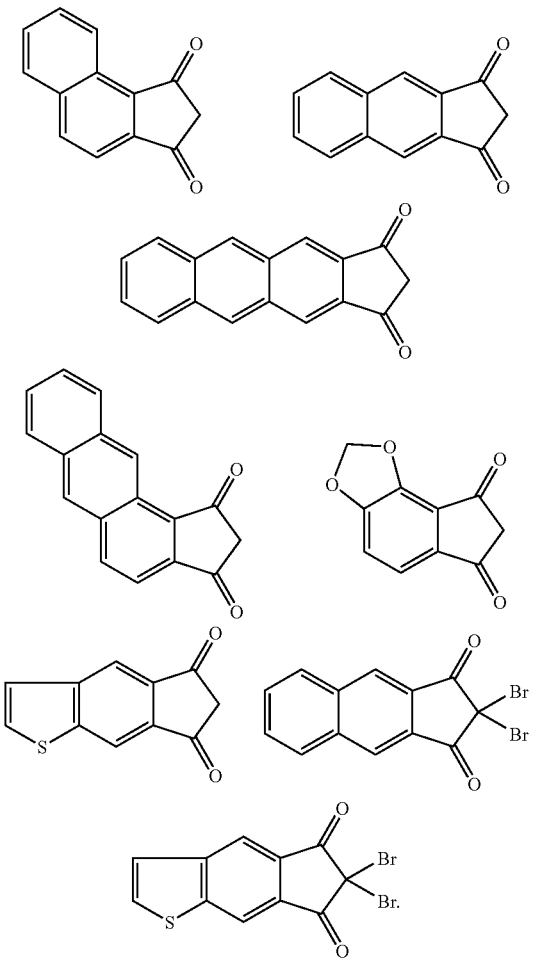

12. The composition according to claim 1, wherein the compounds of formula (II) are chosen from the following compounds:

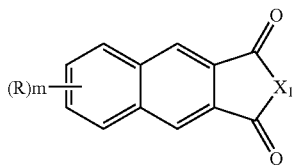

wherein
X₁ is a radical $CR_1R_2$,
wherein $R_1$ and $R_2$, which may be identical or different, are each chosen from a hydrogen atom, halogen atoms, $C_3$-$C_{18}$ alkyl radicals, $C_2$-$C_{18}$ alkenyl radicals, a carboxyl radical, hydroxycarbonylalkyl radicals, hydrogenocarbonyl radicals, hydrogenocarbonylalkyl radicals, alkylcarboxyalkyloxy radicals, a cyano radical, a thiocyano radical, a nitro radical, a nitroso radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, aryl radicals, heteroaryl radicals, and quaternary ammonium radicals, R is chosen from halogen atoms, alkyl radicals, alkenyl radicals, a carboxyl radical, alkoxycarbonyl radicals, hydroxycarbonylalkyl radicals, a hydrogenocarbonyl radical, hydrogenocarbonylalkyl radicals, alkylcarboxylalkyloxy radicals, a cyano radical, a thiocyano radical, a nitro radical, a nitroso radical, a sulphonato radical, alkylsulphonamido radicals, a hydroxyl radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, a silyl radical, C1-C18 alkylsilyl radicals, alkylarylsilyl radicals, arylsilyl radicals, a siloxyl radical, alkylsilyloxy radical, arylsilyloxy radical, aryl radicals, heteroaryl radicals, quaternary ammonium radicals, a radical of the formula

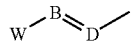

wherein B and D, which may be identical or different, are each chosen from carbon and nitrogen atoms and W is a ring of at least 5 members or an aromatic or heteroaromatic, fused or non-fused polycycle, wherein the heteroatom may be chosen from nitrogen, oxygen, sulphur and phosphorus, and m ranges from 0 to 6.

13. The composition according to claim 12, wherein m is equal to 0 or R is chosen from halogen atoms, alkyl radicals and alkoxy radicals.

14. The composition according to claim 12, wherein $R_1$ and $R_2$, which may be identical or different, are each chosen from a hydrogen atom, halogen atoms, alkyl radicals, and alkoxy radicals.

15. The composition according to claim 1, wherein the compounds of formula (III) are chosen from those of the following formula

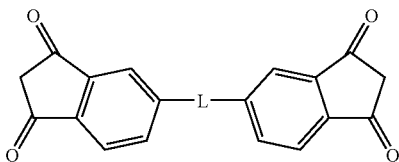

wherein L is a ring of at least 6 members or an aromatic or heteroaromatic, fused or non-fused polycycle, wherein at least one of the rings may be substituted.

16. The composition according to claim 15, wherein L forms a ring fused with at least one of $A_2$ and $A_3$.

17. The composition according to claim 15, wherein the compound of formula (III) is of the following formula:

18. The composition according to claim 1, wherein at least one of the groups L, $R_1$, $R_2$, R, $A_1$, $A_2$ and $A_3$ may be substituted with at least one radical chosen from halo, $C_1$-$C_6$ alkyl, hydroxyl, $C_1$-$C_6$ alkoxy, amino, imidazolyl, pyridinyl, mono($C_1$-$C_6$ alkyl)amino, di($C_1$-$C_6$ alkyl)amino, monohydroxy($C_1$-$C_6$ alkyl)amino, dihydroxy($C_1$-$C_6$ alkyl)amino, tri($C_1$-$C_6$ alkyl)ammmonio, thio, ($C_1$-$C_6$ alkyl)thio, thio($C_1$-$C_6$ alkyl), ($C_1$-$C_6$ alkyl)carbonyl, hydrogenocarbonyl, hydroxycarbonyl, ($C_1$-$C_6$ alkoxy)carbonyl, nitro, and sulphonato radicals and the protonated groups thereof.

19. The composition according to claim 1, further comprising at least one compound chosen from compounds comprising at least one functional group chosen from primary and secondary amino functional groups and compounds comprising at least one activated methylene functional group.

20. The composition according to claim 19, wherein the compounds comprising at least one functional group chosen from primary and secondary amine functional groups are
aromatic amines chosen from
N,N-dimethyl-p-phenylenediamine,
N,N-diethyl-p-phenylenediamine,
N-(2-hydroxyethyl)-N-ethyl-p-phenylenediamine,
N,N-bis(2-hydroxyethyl)-p-phenylenediamine,
N-(2-methoxyethyl)-p-phenylenediamine,
2,3-dichloro-p-phenylenediamine,
,2,4-dichloro-p-phenylenediamine,
2,5-dichloro-p-phenylenediamine,
2-chloro-p-phenylenediamine
dibromohydrate of 2,5-dihydroxy-4-morpholinoaniline,
2-aminophenol,
3-aminophenol,
4-aminophenol,
2-aminomethyl-4-aminophenol,
-2-hydroxymethyl-4-aminophenol,
ortho-phenylenediamine,
para-phenylenediamine,
ortho-toluenediamine,
2,5-diaminotoluene,
2,5-diaminophenol,
2,5-diaminophenethol,
4-amino-3-methylphenol,
2-(2,5-diaminophenyl)ethanol,
2,4-diaminophenoxyethanol,
2-(2,5-diaminophenoxy)ethanol,
4-methylaminoaniline,
3-amino-4-(2'-hydroxyethyloxy)aniline,
3,4-methylenediaminoaniline,
3,4-methylenedioxyaniline,
3-amino-2,4-dichtorophenol,
4-methylaminophenol,
2-methyl-5-aminophenol,
3-methyl-4-aminophenol,
2-methyl-5-(2-hydroxyethylamino)phenol,
6-methyl-3-amino-2-chlorophenol,
2-methyl-5-amino-4-chlorophenol,
3,4-methylenedioxyphenol,
5-(2-hydroxyethylamino)-4-methoxy-2-methylphenol,
4-amino-2-hydroxymethylphenol,
1,3-diamino-2,4-dimethoxybenzene,
2-aminobenzoic acid,
3-aminobenzoic acid,
4-aminobenzoic acid,
2-aminophenylacetic acid,
3-aminophenylacetic acid,
4-aminophenylacetic acid,
2,3-diaminobenzoic acid,
2,4-diaminobenzoic acid,
2,5-diaminobenzoic acid,
3,4-diaminobenzoic acid,
3,5-diaminobenzoic acid,
4-aminosalicylic acid,
5-aminosalicylic acid,
3-amino-4-hydroxybenzoic acid,
4-amino-3-hydroxybenzoic acid,
2-aminobenzenesulphonic acid,
3-aminobenzenesulphonic acid,
4-aminobenzenesulphonic acid,
3-amino-4-hydroxybenzenesulphonic acid,
4-amino-3-hydroxynaphthalene-1-sulphonic acid,
6-amino-7-hydroxynaphthalene-2-sulphonic acid,
7-amino-4-hydroxynaphthalene-2-sulphonic acid,
4-amino-5-hydroxynaphthalene-2,7-disulphonic acid,
3-amino-2-naphthoic acid,
3-aminophthalic acid,
5-aminoisophthalic acid,
1,3,5-triaminobenzene,
1,2,4-triaminobenzene,
1,2,4,5-tetraaminobenzene,
2,4,5-triaminophenol,
pentaaminobenzene,
hexaaminobenzene,
2,4,6-triaminoresorcinol,
4,5-diaminopyrocatechol,
4,6-diaminopyrogallol,
3,5-diamino-4-hydroxypyrocatechol, and
aromatic anilines and aromatic phenols comprising another aromatic residue, corresponding to formula (Ia)

Ia wherein
$R_{1a}$ is chosen from hydroxyl and amino groups optionally substituted with at least one group chosen from $C_1$-$C_4$ alkyl, $C_1$-$C_4$ hydroxyalkyl and ($C_1$-$C_4$ alkoxy)-($C_1$-$C_4$ alkyl) groups,
$R_{2a}$, $R_{3a}$, $R_{4a}$, $R_{5a}$ and $R_{6a}$, which may be identical or different, are each chosen from a hydrogen atom, a hydroxyl group, and an amino group, optionally substituted with at least one group chosen from $C_1$-$C_4$ alkyl, $C_1$-$C_4$ hydroxyalkyl, and ($C_1$-$C_4$ alkoxy)-($C_1$-$C_4$ alkyl) groups, and carboxylic and sulphonic acid groups,
Z is chosen from a direct bond, a $C_1$-$C_4$ hydrocarbon chain which is saturated or unsaturated and optionally hydroxylated, a carbonyl, sulphonyl or imino group, an oxygen or sulphur atom, and a group of formula Q-(CH₂—P—CH₂-Q')ₒ wherein P is a direct bond or a group —CH₂— or —CHOH—, Q and Q', which may be identical or different, are each chosen from an oxygen atom, a group NR₇ wherein R₇ is chosen from a hydrogen atom, and $C_1$-$C_4$ alkyl and $C_1$-$C_4$ hydroxyalkyl groups and groups O—(CH₂)$_p$NH and NH—(CH₂)$_{p'}$—O wherein p and p', which may be identical or different, are each 2 or 3, and o is a number ranging from 1 to 4, and aliphatic amines chosen from
2-aminoethanol,
2-methoxyethylamine,
2-ethoxyethylamine,
2-(2-aminoethoxy)ethanol,
2-or 3-aminopropanol,
2,3-dihydroxypropylamine,
4-hydroxypropylamine,
2-aminopropane-1,3-diol,
2-amino-2-methylpropanol,
2-amino-2-methylpropane-1,3-diol,
2-amino-2-hydroxymethylpropane-1,3-diol,
tetrahydropentylamine,
pentahydroxyhexylamines,
1,2-diaminoethane,
1,2-diaminopropane,
1,3-diaminopropane,
1,3-diamino-2-propanol,
2-(2-aminoethylamino)ethylamine,
2-(2-aminoethylamino)ethanol,
3-(2-aminoethylamino)propylamine and
3-(2-aminoethylamino)propanol.

21. The composition according to claim 19, wherein the compounds comprising at least one activated methylene functional group are chosen from
1,2,3,3-tetramethyl-3H-indolium iodide,
1,2,3,3-tetramethyl-3H-indolium p-toluenesulphonate,
1,2,3,3-tetramethyl-3H-indolium methanesulphonate,
1,3,3-trimethyl-2-methyleneindoline,
2,3-dimethylbenzothiazolium iodide,
2,3-dimethylbenzothiazolium p-toluenesulphonate,
rhodanine,
rhodanine-acetic acid,
1-ethyl-2-quinaldinium iodide,
1-methyl-2-quinaldinium iodide,
barbituric acid,
thiobarbituric acid,
1,3-dimethylthiobarbituric acid,
diethylthiobarbituiric acid,
oxindole,
3-indoxyl acetate,
coumarin and
1-methyl-3-phenyl-2-pyrazinone.

22. The composition according to claim 1, wherein the composition has a pH ranging from 2 to 12.

23. The composition according to claim 22, wherein the composition has a pH ranging from 6 to 11.

24. The composition according to claim 1, wherein the at least one 1,3-indandione derivative chosen from compounds of formulae (I), (II) and (III) is present in an amount ranging from 0.0001% to 30% by weight, relative to the total weight of the composition.

25. The composition according to claim 19, wherein the at least one compound chosen from compounds comprising at least one activated methylene functional group and compounds comprising at least one functional group chosen from primary and secondary amine functional groups is present in an amount ranging from 0.0001% to 30% by weight, relative to the total weight of the composition.

26. The composition according to claim 1, further comprising at least one additional ingredient chosen from nonionic, cationic, anionic and amphoteric surfactants and from nonionic, cationic, anionic and amphoteric polymeric agents.

27. A multicomponent dyeing agent, comprising
as a first component, a composition (a) comprising at least one 1,3-indandione derivative chosen from compounds of formulae (I), (II) and (III)

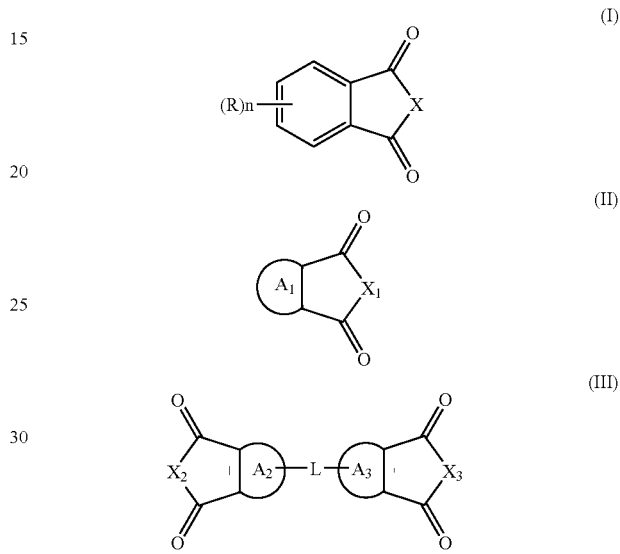

wherein
X, $X_1$, $X_2$ and $X_3$, which may be identical or different, are each a radical $CR_1R_2$,
wherein $R_1$ and $R_2$, which may be identical or different, are each chosen from a hydrogen atom, halogen atoms, $C_3$-$C_{18}$ alkyl radicals, $C_2$-$C_{18}$ alkenyl radicals, a carboxyl radical, hydroxycarbonylalkyl radicals, hydrogenocarbonyl radicals, hydrogenocarbonylalkyl radicals, alkylcarboxyalkyloxy radicals, a cyano radical, a thiocyano radical, a nitro radical, a nitroso radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, aryl radicals, heteroaryl radicals, and quaternary ammonium radicals, $A_1$ is chosen from fused and non-fused polyaromatic radicals comprising from 6 to 50 carbon atoms, which may comprise at least one heteroatom chosen from nitrogen, sulphur, oxygen, and phosphorus, $A_2$ and $A_3$, which may be identical or different, are each chosen from fused and non-fused, mono- and polyaromatic radicals comprising from 6 to 50 carbon atoms, which may comprise at least one heteroatom chosen from nitrogen, sulphur, oxygen, and phosphorus, L is a single bond or an aliphatic or aromatic divalent radical, which may comprise at least one heteroatom chosen from oxygen, sulphur, nitrogen and phosphorus and may be fused with at least one of $A_2$ and $A_3$;

n is an integer chosen from 0,1, 2, 3, and 4,

R is chosen from halogen atoms, alkyl radicals, alkenyl radicals, a carboxyl radical, alkoxycarbonyl radicals, hydroxycarbonylalkyl radicals, a hydrogenocarbonyl radical, hydrogenocarbonylalkyl radicals, alkylcarboxylalkyloxy radicals, a cyano radical, a thiocyano radical, a nitro radical, a nitroso radical, a sulphonato radical, alkylsulphonamido radicals, a hydroxyl radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, a silyl radical, $C_1$-$C_{18}$ alkylsilyl radicals, alkylarylsilyl radicals, arylsilyl radicals, a siloxyl radical, alkylsilyloxy radical, arylsilyloxy radical, aryl radicals, heteroaryl radicals, quaternary ammonium radicals, a radical of the formula

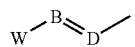

wherein B and D, which may be identical or different, are each chosen from carbon and nitrogen atoms and W is a ring of at least 5 members or an aromatic or heteroaromatic, fused or non-fused polycycle, wherein the heteroatom may be chosen from nitrogen, oxygen, sulphur and phosphorus, with the following provisos when X is a radical $CR_1R_2$ and $R_1$ and $R_2$ are each a hydrogen atom, the compound of formula (I) is of the following formula:

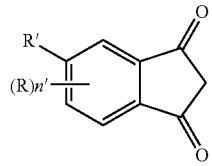

wherein n' is equal to 0, 1, 2 or 3, and R' is as defined for R but is not a methoxy radical or a chloro radical, when X is a radical $CR_1R_2$, n is equal to 0 and $R_1$ is a hydrogen atom, then $R_2$ is chosen from halogen atoms and substituted alkyl radicals comprising from 1 to 4 carbon atoms, and when X is a radical $CR_1R_2$, n is equal to 0 and $R_1$ is OH, then $R_2$ is not an amino, alkylamino, dialkylamino, arylalkylamino, diarylamino or alkenylamino radical, and as a second component, a composition (b) comprising at least one activator which makes it possible to modify the kinetics of reaction of the at least one 1,3-indandione derivative.

28. An agent according to claim 27, wherein the at least one activator is chosen from compounds comprising at least one functional group chosen from primary and secondary amine functional groups and compounds comprising at least one activated methylene functional group.

29. A method for dyeing keratin material, comprising applying a dyeing composition to a keratin material for a leave-in time sufficient to allow a desired color to be obtained, wherein the dyeing composition comprises, in an appropriate medium, at least one 1,3-indandione derivative chosen from compounds of formulae (I), (II) and (III)

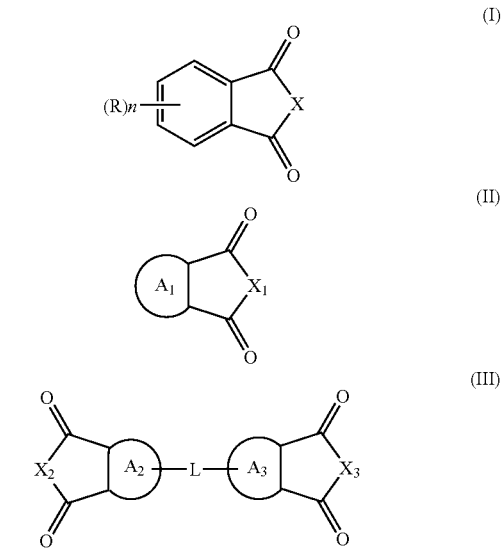

wherein $X$, $X_1$, $X_2$ and $X_3$, which may be identical or different, are each a radical $CR_1R_2$, wherein $R_1$ and $R_2$, which may be identical or different, are each chosen from a hydrogen atom, halogen atoms, $C_3$-$C_{18}$ alkyl radicals, $C_2$-$C_{18}$ alkenyl radicals, a carboxyl radical, hydroxycarbonylalkyl radicals, hydrogenocarbonyl radicals, hydrogenocarbonylalkyl radicals, alkylcarboxyalkyloxy radicals, a cyano radical, a thiocyano radical, a nitro radical, a nitroso radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, aryl radicals, heteroaryl radicals, and quaternary ammonium radicals, $A_1$ is chosen from fused and non-fused polyaromatic radicals comprising from 6 to 50 carbon atoms, which may comprise at least one heteroatom chosen from nitrogen, sulphur, oxygen, and phosphorus, $A_2$ and $A_3$, which may be identical or different, are each chosen from fused and non-fused, mono- and polyaromatic radicals comprising from 6 to 50 carbon atoms, which may comprise at least one heteroatom chosen from nitrogen, sulphur, oxygen, and phosphorus, L is a single bond or an aliphatic or aromatic divalent radical, which may comprise at least one heteroatom chosen from oxygen, sulphur, nitrogen and phosphorus and may be fused with at least one of $A_2$ and $A_3$;

n is an integer chosen from 0, 1, 2, 3, and 4,

R is chosen from halogen atoms, alkyl radicals, alkenyl radicals, a carboxyl radical, alkoxycarbonyl radicals, hydroxycarbonylalkyl radicals, a hydrogenocarbonyl radical, hydrogenocarbonylalkyl radicals, alkylcarboxylalkyloxy radicals, a cyano radical, a thiocyano radical, a nitro radical, a nitroso radical, a sulphonato radical, alkylsulphonamido radicals, a hydroxyl radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, a silyl radical, $C_1$-$C_{18}$ alkylsilyl radicals, alkylarylsilyl radicals, arylsilyl radicals, a siloxyl radical, alkylsilyloxy radical, arylsilyloxy radical, aryl radicals, heteroaryl radicals, quaternary ammonium radicals, a radical of the formula

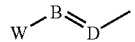

wherein B and D, which may be identical or different, are each chosen from carbon and nitrogen atoms and W is a ring of at least 5 members or an aromatic or heteroaromatic, fused or non-fused polycycle, wherein the heteroatom may be chosen from nitrogen, oxygen, sulphur and phosphorus, with the following provisos when X is a radical $CR_1R_2$ and $R_1$ and $R_2$ are each a hydrogen atom, the compound of formula (I) is of the following formula:

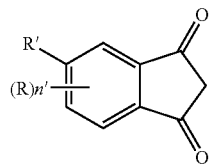

wherein n' is equal to 0, 1, 2 or 3, and R' is as defined for R but is not a methoxy radical or a chloro radical, when X is a radical $CR_1R_2$, n is equal to 0 and $R_1$ is a hydrogen atom, then $R_2$ is chosen from halogen atoms and substituted alkyl radicals comprising from 1 to 4 carbon atoms, and when X is a radical $CR_1R_2$, n is equal to 0 and $R_1$ is OH, then $R_2$ is not an amino, alkylamino, dialkylamino, arylalkylamino, diarylamino or alkenylamino radical.

30. The dyeing method according to claim 29, further comprising heating the keratin material to which the dyeing composition is applied to a temperature of less than or equal to 250° C.

31. The dyeing method according to claim 30, further comprising heating the keratin material to which the dyeing composition is applied to a temperature of less than or equal to 60° C.

32. A method for dyeing keratin material, comprising applying to a keratin material, one after the other, in any order, a composition (a) and a composition (b), wherein the composition (a) comprises at least one 1,3-indandione derivative chosen from compounds of formulae (I), (II) and (III)

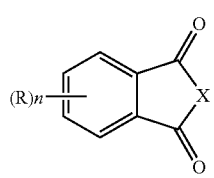

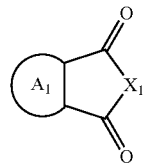

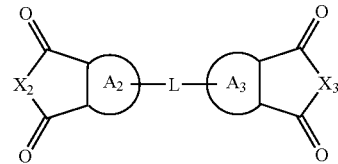

wherein

X, $X_1$, $X_2$ and $X_3$, which may be identical or different, are each a radical $CR_1R_2$, wherein $R_1$ and $R_2$, which may be identical or different, are each chosen from a hydrogen atom, halogen atoms, $C_3$-$C_{18}$ alkyl radicals, $C_2$-$C_{18}$ alkenyl radicals, a carboxyl radical, hydroxycarbonylalkyl radicals, hydrogenocarbonyl radicals, hydrogenocarbonylalkyl radicals, alkylcarboxyalkyloxy radicals, a cyano radical, a thiocyano radical, a nitro radical, a nitroso radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, aryl radicals, heteroaryl radicals, and quaternary ammonium radicals, $A_1$ is chosen from fused and non-fused polyaromatic radicals comprising from 6 to 50 carbon atoms, which may comprise at least one heteroatom chosen from nitrogen, sulphur, oxygen, and phosphorus, $A_2$ and $A_3$, which may be identical or different, are each chosen from fused and non-fused, mono- and polyaromatic radicals comprising from 6 to 50 carbon atoms, which may comprise at least one heteroatom chosen from nitrogen, sulphur, oxygen, and phosphorus, L is a single bond or an aliphatic or aromatic divalent radical, which may comprise at least one heteroatom chosen from oxygen, sulphur, nitrogen and phosphorus and may be fused with at least one of $A_2$ and $A_3$;

n is an integer chosen from 0, 1, 2, 3, and 4,

R is chosen from halogen atoms, alkyl radicals, alkenyl radicals, a carboxyl radical, alkoxycarbonyl radicals, hydroxycarbonylalkyl radicals, a hydrogenocarbonyl radical, hydrogenocarbonylalkyl radicals, alkylcarboxylalkyloxy radicals, a cyano radical, a thiocyano radical, a nitro radical, a nitroso radical, a sulphonato radical, alkylsulphonamido radicals, a hydroxyl radical, hydroxyalkyl radicals, alkoxy radicals, alkenyloxy radicals, aryloxy radicals, an amino radical, alkylamino radicals, dialkylamino radicals, arylalkylamino radicals, diarylamino radicals, alkenylamino radicals, a thio radical, alkylthio radicals, arylthio radicals, alkenylthio radicals, a silyl radical, $C_1$-$C_{18}$ alkylsilyl radicals, alkylarylsilyl radicals, arylsilyl radicals, a siloxyl radical, alkylsilyloxy radical, arylsilyloxy radical, aryl radicals, heteroaryl radicals, quaternary ammonium radicals, a radical of the formula

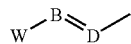

wherein B and D, which may be identical or different, are each chosen from carbon and nitrogen atoms and W is a ring of at least 5 members or an aromatic or heteroaromatic, fused or non-fused polycycle, wherein the heteroatom may be chosen from nitrogen, oxygen, sulphur and phosphorus, with the following provisos when X is a radical $CR_1R_2$ and $R_1$ and $R_2$ are each a hydrogen atom, the compound of formula (I) is of the following formula:

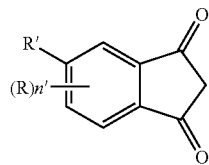

wherein n' is equal to 0,1, 2 or 3, and R' is as defined for R but is not a methoxy radical or a chloro radical, when X is a radical $CR_1R_2$, n is equal to 0 and $R_1$ is a hydrogen atom, then $R_2$ is chosen from halogen atoms and substituted alkyl radicals comprising from 1 to 4 carbon atoms, and when X is a radical $CR_1R_2$, n is equal to 0 and $R_1$ is OH, then $R_2$ is not an amino, alkylamino, dialkylamino, arylalkylamino, diarylamino or alkenylamino radical, and the composition (b) comprises at least one activator which makes it possible to modify the kinetics of reaction of the at least one 1,3-indandione derivative.

33. The dyeing method according to claim 32, further comprising rinsing the keratin material between the application of the composition (a) and the application of the composition (b).

34. The dyeing method according to claim 29, wherein the keratin material is keratin fibers.

35. The dyeing method according to claim 32, wherein the keratin material is keratin fibers.

* * * * *